United States Patent [19]

Merger et al.

[11] Patent Number: 5,166,447
[45] Date of Patent: Nov. 24, 1992

[54] PREPARATION OF CYCLOPENTANONES

[75] Inventors: Franz Merger, Frankenthal; Tom Witzel, Ludwigshafen, both of Fed. Rep. of Germany

[73] Assignee: BASF Aktiengesellschaft, Ludwigshafen, Fed. Rep. of Germany

[21] Appl. No.: 776,688

[22] Filed: Oct. 15, 1991

Related U.S. Application Data

[63] Continuation of Ser. No. 520,039, May 7, 1990, abandoned.

[30] Foreign Application Priority Data

May 18, 1989 [DE] Fed. Rep. of Germany ....... 3916138
May 18, 1989 [DE] Fed. Rep. of Germany ....... 3916139
May 18, 1989 [DE] Fed. Rep. of Germany ....... 3916140

[51] Int. Cl.[5] ............................................. C07C 45/60
[52] U.S. Cl. ................................... 568/341; 568/343; 568/347
[58] Field of Search .................... 568/341, 343, 347

[56] References Cited

U.S. PATENT DOCUMENTS

| | | | |
|---|---|---|---|
| 2,479,284 | 8/1949 | Whetstone et al. | 549/425 |
| 2,694,077 | 11/1954 | Stansbury et al. | 568/347 |
| 2,823,211 | 2/1958 | Guest et al. | 568/347 |
| 2,863,923 | 12/1958 | Bortnick | 568/347 |
| 2,875,249 | 2/1959 | Stansbury et al. | 568/347 |
| 2,995,607 | 8/1961 | Klemchuk | 568/347 |
| 3,812,190 | 5/1974 | Petrovich et al. | 568/347 |
| 4,822,920 | 4/1989 | Lermer et al. | 568/347 |

FOREIGN PATENT DOCUMENTS 0266687 11/1988 European Pat. Off. ............ 568/347

OTHER PUBLICATIONS

Synthesis (1983) 796–797.
J. Am. Chem. Soc. vol. 67 (1945) 1745–1754.
J. Am. Chem. Soc. vol. 53 (1931) 3160–3164.
Bull. Chem. Jpn. vol. 54 (1981) 3875–3876.
Tetrahedron Lett. (1968) 1003–1006.
Bull. Soc. Chim. Fr. (1957) 1064–1069.
Houben-Weyl, vol. 6, Part 4 (1966) 373–374.

Primary Examiner—James H. Reamer
Attorney, Agent, or Firm—John H. Shurtleff

[57] ABSTRACT

Cyclopentanones of the general formula I

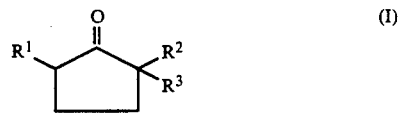

where $R^1$ and $R^2$ are each an organic radical or $R^1$ or $R^2$ may be hydrogen and $R^3$ is hydrogen or formyl, are prepared by a process in which a 2-formyl-3,4-dihydropyran of the general formula II

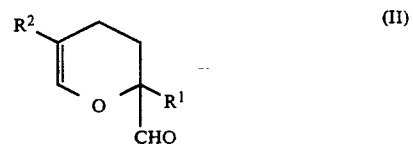

where $R^1$ and $R^2$ have the abovementioned meanings,
  a) where $R^3$ is formyl, is converted in the presence of an acidic heterogeneous catalyst at from 50° to 500° C., and
  b) where $R^3$ is hydrogen,
    b₁) is reacted with water or an alcohol in the presence of an acidic heterogeneous catalyst at from 100° to 500° C. in the gas phase or
    b₂) a compound II or an acrolein of the general formula III

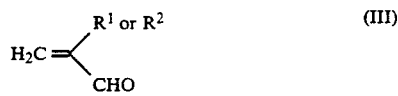

is reacted with water or with water in the presence of an acid or with an alcohol in the presence of an acid at from 150° to 400° C. in the liquid phase. Novel 2-formylcyclopentanones are obtained.

17 Claims, No Drawings

PREPARATION OF CYCLOPENTANONES

This application is a continuation of application Ser. No. 520,039 filed May 7, 1990, now abandoned.

The present invention relates to novel and improved processes for the acid-catalyzed preparation of cyclopentanones from 2-formyl-3,4-dihydropyrans or from acroleins, and novel 2,5-disubstituted 2-formylcyclopentanones.

Synthesis (1983), 796-797 discloses that 2-formylcyclopentanone can be prepared by condensation of cyclopentanone with a formic ester in the presence of potassium hydride. The base used may be, for example, sodium methylate (J. Am. Chem. Soc. 67 (1945), 1745-1754) or sodium (J. Am. Chem. Soc. 53 (1931), 3160-3164.

U.S. Pat. No. 2,875,249 discloses that 2,5-dimethylcyclopentanone can be prepared by a batchwise method by reacting 2,5-dimethyl-2-formyl-3,4-dihydropyran (dimeric methacrolein) with an excess of hydrochloric or sulfuric acid (from 20 to 50% strength in water) at from 110° to 125° C., a ketone/water mixture being distilled off. The yield decreases from 44% to 23% if less than the stoichiometric amount of mineral acid is used.

Bull. Chem. Jpn. 54 (1981), 3875-3876 discloses the reaction of n-alkanals with an excess of formaldehyde and stoichiometric amounts of dimethylammonium hydrochloride in dioxane/formic acid at 200° C. to give 2,5-dialkylcyclopentanone in a maximum yield of 26%.

2,5-Disubstituted cyclopentanones may furthermore be prepared by:

cyclization of 2,5-disubstituted adipic diesters in the gas phase over heterogeneous catalysts, for example 2,5-dimethylcyclopentanone from dimethyl 2,5-dimethyladipate over $MnO_2/Al_2O_3$ (U.S. Pat. No. 2,863,923), formylation of dienes under catalysis by a metal carbonyl, for example 2,5-dimethylcyclopentanone from 1,5-hexadiene using $Co_2(CO)_8$ according to U.S. Pat. No. 2,995,607 or using $Ni(CO)_4$ according to Tetrahedron Lett. (1968), 1003-1006, or alkylation of cyclopentanone, for example with dimethyl sulfate, to give mainly 2,2-dimethylcyclopentanone and only small amounts of 2,5-dimethylcyclopentanone (Bull. Soc. Chim. Fr. (1957), 1064-1069).

U.S. Pat. No. 3,812,190 discloses that the dimer of unsubstituted acrolein (2-formyl-3,4-dihydropyran) can be converted in the gas phase at from 200° to 350° C. over dehydrogenation catalysts (CuO, NiO, CoO or Pd), alone or on acidic carriers, such as silica or alumina, into cyclopentanone; at a reaction temperature of 225° C. and a conversion of 70%, the selectivity is stated as not less than 80%. However, only unsatisfactory yields are obtained when the process is applied to the dimers of α-substituted acroleins. In attempts to use the stated catalysts, such as $Pd/Al_2O_3$ or NiO, for the preparation of, for example, dimethylcyclopentanone from 2-formyl-2,5-dimethyl-3,4-dihydropyran (dimeric methacrolein), selectivities of less than 20% were achieved under conditions described in U.S. Pat. No. 3,812,190. Furthermore, U.S. Pat. Nos. 2,694,077 and 2,823,211 disclose that formyldihydropyrans react with water under acid catalysis (mineral acids, carboxylic acids) to give a mixture of adipodialdehydes and hydroxytetrahydropyrans or to give dialkylhydroxycaprolactones and, according to Houben-Weyl, vol. 6, Part 4, pages 373-374 (1966), can be reacted with alcohols, e.g. methanol, to give 6-methoxy-2,5-dialkyl-2-dimethoxymethyltetrahydropyran as a mixture with a number of byproducts, including bicyclic derivatives.

The disadvantages of the conventional processes for the preparation of 2,5-disubstituted cyclopentanones are low yields in conjunction with a technically involved procedure or the use of expensive starting materials.

It is an object of the present invention to provide processes which make it possible to obtain even substituted cyclopentanones and 2-formylcyclopentanones in a simple manner.

We have found that this object is achieved by novel and improved processes for the preparation of cyclopentanones of the general formula I

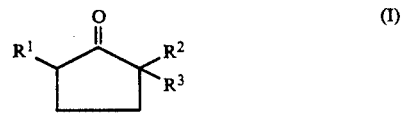

where $R^1$ and $R^2$ are each an organic radical or either of $R^1$ or $R^2$ may be hydrogen and $R^3$ is hydrogen or formyl, wherein a 2-formyl-3,4-dihydropyran of the general formula II

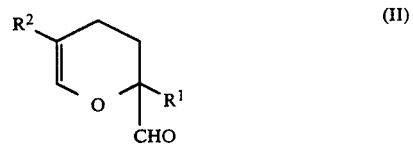

where $R^1$ and $R^2$ have the abovementioned meanings, a) where $R^3$ is formyl, is converted in the presence of an acidic heterogeneous catalyst at from 50° to 500° C., and b) where $R^3$ is hydrogen, b₁) is reacted with water or an alcohol in the presence of an acidic heterogeneous catalyst at from 100° to 500° C. in the gas phase or b₂) a compound II or an acrolein of the general formula III

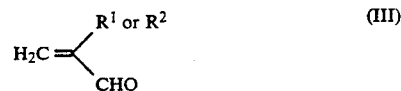

in which both $R^1$ and $R^2$ must be an organic radical, is reacted with water or with water in the presence of an acid or with an alcohol in the presence of an acid at from 150° to 400° C. in the liquid phase.

We have furthermore found novel 2,5-disubstituted 2-formylcyclopentanones.

a) Where $R^3$ is formyl, the 2-formylcyclopentanones are obtainable by the following method:

The isomerization of 2-formyl-3,4-dihydropyrans II to give 2-formylcyclopentanone I is carried out by contact with acidic catalysts, preferably acidic heterogeneous catalysts, essentially in the absence of water or of alcohol.

Decarbonylation of the formylcyclopentanones ($R^3$=CHO) I to cyclopentanones ($R^3$=H) I is observed only to an insignificant extent in the novel process.

The reaction can be carried out both in the liquid phase and as a batchwise or, preferably, continuous gas phase reaction at from 50° to 500° C. and under from 0.01 mbar to 10 bar. The use of an inert solvent, e.g. cyclohexane or petroleum ether, may be advantageous.

The liquid phase reaction can be carried out, for example, as a suspension or trickle-bed reaction at from 50° to 400° C., preferably from 70° to 300° C., under atmospheric, superatmospheric or reduced pressure.

The preferred gas phase reaction can be carried out, for example, at from 100° to 500° C., preferably from 100° to 400° C., and under from 0.1 mbar to 10 bar, particularly preferably at from 200° to 300° C. and under from 0.5 mbar to 2 bar. In the reaction in the gas phase, a weight hourly space velocity (WHSV) of from 0.01 to 40, in particular from 0.05 to 10, g of starting material of the formula II per g of catalyst per hour is advantageously maintained. The gas phase reaction can be carried out in a fixed bed or in a fluidized bed.

The process is carried out in general under atmospheric pressure or, depending on the volatility of the starting compound, under reduced or superatmospheric pressure, preferably by a continuous procedure.

Sparingly volatile or solid starting materials are used in dissolved form, for example in solution in tetrahydrofuran, toluene or petroleum ether. In general, dilution with these solvents or with inert gases, such as $N_2$ or Ar, is also possible and advantageous.

After the reaction, the products formed are isolated from the reaction mixture by conventional methods, for example by distillation; unconverted starting materials may be recycled to the reaction.

Preferably, reaction products are immediately fed to a separation stage and are separated into their individual components, for example in a fractionation column.

The 2-formyl-3,4-dihydropyrans II are obtainable by heating $\alpha$-substituted acroleins III (Houben-Weyl, Vol. VII, Part 1, pages 130-131, U.S. Pat. Nos. 2,479,283 and 2,479,284), in accordance with the following equation, where $R^1$ and $R^2$ may be identical or different:

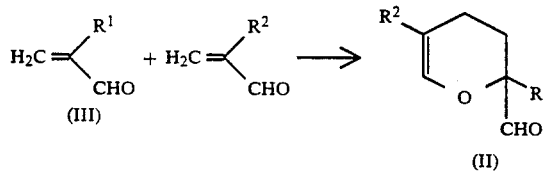

The acroleins III can be prepared in high yield, for example according to EP-A-58927, by condensation of alkanals with formaldehyde.

Suitable acidic heterogeneous catalysts for the novel process are acidic oxides which essentially consist of oxides of main groups II to V or of subgroups III to VII, of oxides of the rare earth metals or of a mixture of the stated oxides. For example, boron oxide, alumina, silica, for example in the form of silica gel, kieselguhr or quartz, tin dioxide, titanium dioxide, cerium oxide or a mixture of such oxides are suitable. The catalysts may be additionally modified by applying additives, such as phosphoric acid. Other suitable catalysts are phosphates, such as aluminum phosphates or silicon aluminum phosphates. Silica-containing catalysts are preferred. The use of silica has proven very particularly useful.

Zeolites are also suitable.

The catalysts can be used in the form of 2-4 mm extrudates or as pellets having a diameter of from 3 to 5 mm, as chips having particle sizes of from 0.05 to 1 mm, in particular from 0.1 to 0.5 mm, as powder having particle sizes of 0.1 to 0.5 mm or as a fluidizable catalyst.

$R^1$ and $R^2$ in the compounds I and II have the following meanings for the novel process, where either $R^1$ or $R^2$ (but not both) may furthermore be hydrogen:

straight-chain or branched $C_1$-$C_{10}$-alkyl, preferably $C_1$-$C_8$-alkyl, particularly preferably $C_1$-$C_4$-alkyl, such as methyl, ethyl, n-propyl, isopropyl, n-butyl, isobutyl, sec-butyl or tert-butyl, straight-chain or branched $C_1$-$C_{10}$-alkyl which is substituted by cycloaliphatic radicals, such as cycloalkyl, aromatic radicals, such as aryl, in particular phenyl, or heterocyclic radicals, such as pyridyl, by an alkenyl or alkynyl radical or by carbalkoxy, carboxyl, alkylamino, acyl, phosphonic ester, hydroxyl, ether, cycloether, thioether or cyclothioether groups, preferably $C_3$-$C_8$-cycloalkyl, $C_1$-$C_4$-carbalkoxy or $C_2$-$C_4$-alkenyl, particularly preferably $C_5$- or $C_6$-cycloalkyl and $C_1$-$C_7$-carbalkoxy.

Preferred compounds I and II are those in which $R^1$ and $R^2$ are not hydrogen, preferred compounds here in turn being those in which $R^1 = R^2$.

In the novel 2,5-disubstituted 2-formylcyclopentanones I, $R^1$ and $R^2$ have the same meaning.

Starting materials of the formula II are, for example:
2,5-dimethyl-2-formyl-3,4-dihydropyran
2,5-diethyl-2-formyl-3,4-dihydropyran
2,5-di-n-propyl-2-formyl-3,4-dihydropyran
2,5-di-isopropyl-2-formyl-3,4-dihydropyran
2,5-di-n-butyl-2-formyl-3,4-dihydropyran
2,5-di-(3-methoxycarbonylpropyl)-2-formyl-3,4-dihydropyran
2,5-di-(methoxycarbonylmethyl)-2-formyl-3,4-dihydropyran
2-methyl-2-formyl-3,4-dihydropyran
5-methyl-2-formyl-3,4-dihydropyran
2,5-di-(2-propenyl)-2-formyl-3,4-dihydropyran.

End products of the formula I are, for example:
2,5-dimethyl-2-formylcyclopentanone
2,5-diethyl-2-formylcyclopentanone
2,5-di-n-propyl-2-formylcyclopentanone
2,5-di-isopropyl-2-formylcyclopentanone
2,5-di-n-butyl-2-formylcyclopentanone
2,5-di-(3-methoxycarbonylpropyl)-2-formylcyclopentanone
2,5-di-(methoxycarbonylmethyl)-2-formylcyclopentanone
2-methyl-2-formylcyclopentanone
5-methyl-2-formylcyclopentanone
2,5-di-(propenyl)-2-formylcyclopentanone Novel 2-formylcyclopentanones I are:
2,5-dimethyl-2-formylcyclopentanone
2,5-diethyl-2-formylcyclopentanone
2,5-di-n-propyl-2-formylcyclopentanone
2,5-di-isopropyl-2-formylcyclopentanone
2,5-di-n-butyl-2-formylcyclopentanone
2,5-di-(3-methoxycarbonylpropyl)-2-formylcyclopentanone
2,5-di-(methoxycarbonylmethyl)-2-formylcyclopentanone The 2-formylcyclopentanones I are suitable, for example, as solvents or as intermediates for the synthesis of scents, drugs and plastics precursors.

b) Where $R^3$ is hydrogen, the cyclopentanones I are obtainable by the following methods:

b₁) 2-Formyl-3,4-dihydropyrans II are reacted with water or with an alcohol over acidic heterogeneous catalysts, in accordance with the following equation:

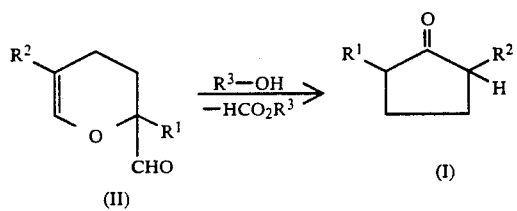

The reaction can be carried out batchwise or, preferably, continuously in the gas phase at from 100° to 500° C. and under from 0.1 mbar to 10 bar.

The gas phase reaction can be effected, for example, at from 100° to 450° C., preferably from 100° to 350° C., and under from 0.1 mbar to 5 bar, particularly preferably at from 200° to 300° C. and under from 0.5 mbar to 2 bar. In the reaction in the gas phase, a weight hourly space velocity of from 0.01 to 40, in particular from 0.05 to 10, g of starting material of the formula II per g of catalyst per hour is advantageously maintained. The gas phase reaction can be carried out in a fixed bed or in a fluidized bed.

The process is carried out in general under atmospheric pressure or, depending on the volatility of the starting compound, under reduced or superatmospheric pressure, preferably by a continuous procedure.

The molar ratio of water or alcohol to the 2-formyl-3,4-dihydropyran II is from 0.5:1 to 20:1, preferably from 1:1 to 10:1, particularly preferably from 2:1 to 7:1.

Suitable alcohols are those of 1 to 20, preferably 1 to 8, particularly preferably 1 to 4, carbon atoms, such as methanol and ethanol.

Sparingly volatile or solid starting materials are used in dissolved form, for example in solution in tetrahydrofuran, toluene or petroleum ether. In general, dilution with these solvents or with inert gases, such as N₂ or Ar, is also possible and advantageous.

2-Formylcyclopentanones of the formula I with (R=CHO) may be formed as byproducts, and formation of these byproducts can be virtually completely suppressed by suitable measures, such as increasing the temperature or increasing the amount of water/alcohol added or reducing the space velocity.

After the reaction, the products formed are isolated from the reaction mixture by conventional methods, for example by distillation; unconverted starting materials may be recycled to the reaction.

Reaction products are preferably immediately fed to a separation stage and are separated into their individual components, for example in a fractionation column.

Suitable acidic heterogeneous catalysts for the novel process are acidic oxides which essentially consist of oxides of main groups II to V or of subgroups III to VII, of oxides of the rare earth metals or of a mixture of the stated oxides. For example, boron oxide, alumina, silica, for example in the form of silica gel, kieselguhr or quartz, tin dioxide, titanium dioxide, cerium oxide or a mixture of such oxides are suitable. The catalysts may be additionally modified by applying additives, such as phosphoric acid. Other suitable catalysts are phosphates, such as aluminum phosphates or silicon aluminum phosphates. Silica-containing catalysts are preferred. The use of silica has proven very particularly useful.

Zeolites are also suitable.

The catalysts can be used in the form of 2–4 mm extrudates or as pellets having a diameter of from 3 to 5 mm, as chips having particle sizes of from 0.05 to 1 mm, in particular from 0.1 to 0.5 mm, as powder having particle sizes of 0.1 to 0.5 mm or as a fluidizable catalyst.

$R^1$ and $R^2$ in the compounds I and II have the following meanings for the novel process, where either $R^1$ or $R^2$ may furthermore be hydrogen:

straight-chain or branched $C_1$–$C_{10}$-alkyl, preferably $C_1$–$C_8$-alkyl, particularly preferably $C_1$–$C_4$-alkyl, such as methyl, ethyl, n-propyl, isopropyl, n-butyl, isobutyl, sec-butyl or tert-butyl, straight-chain or branched $C_1$–$C_{10}$-alkyl which is substituted by cycloaliphatic radicals, such as cycloalkyl, aromatic radicals, such as aryl, in particular phenyl, or heterocyclic radicals, such as pyridyl, by an alkenyl or alkynyl radical or by carbalkoxy, carboxyl, alkylamino, acyl, phosphonic ester, hydroxyl, ether, cycloether, thioether or cyclothioether groups, preferably $C_3$–$C_8$-cycloalkyl, $C_1$–$C_4$-carbalkoxy, carboxyl, or $C_2$–$C_4$-alkenyl, particularly preferably $C_5$- or $C_6$-cycloalkyl and $C_1$–$C_3$-carbalkoxy.

Preferred compounds I and II are those in which $R^1$ and $R^2$ are not hydrogen, preferred compounds here in turn being those in which $R^1 = R^2$.

Starting materials of the formula II are, for example:
2,5-dimethyl-2-formyl-3,4-dihydropyran
2,5-diethyl-2-formyl-3,4-dihydropyran
2,5-di-n-propyl-2-formyl-3,4-dihydropyran
2,5-di-isopropyl-2-formyl-3,4-dihydropyran
2,5-di-n-butyl-2-formyl-3,4-dihydropyran
2,5-di-(3-methoxycarbonylpropyl)-2-formyl-3,4-dihydropyran
2,5-di-(methoxycarbonylmethyl)-2-formyl-3,4-dihydropyran
2-methyl-2-formyl-3,4-dihydropyran
5-methyl-2-formyl-3,4-dihydropyran
2,5-di-(2-propenyl)-2-formyl-3,4-dihydropyran.

End products of the formula I are, for example:
2,5-dimethylcyclopentanone
2,5-diethylcyclopentanone
2,5-di-n-propylcyclopentanone
2,5-di-isopropylcyclopentanone
2,5-di-n-butylcyclopentanone
2,5-di-(3-methoxycarbonylpropyl)-cyclopentanone
2,5-di-(methoxycarbonylmethyl)-cyclopentanone
2-methyl-cyclopentanone
2,5-di-(2-propenyl)-cyclopentanone b₂) The reaction of the 2-formyl-3,4-dihydropyrans or of the acroleins with water or with water in the presence of an acid or with an alcohol in the presence of an acid can be carried out batchwise or, preferably, continuously in the liquid phase at from 150° to 400° C., preferably at from 200° to 300° C. and under from 1 to 200 bar, particularly preferably at from 230° to 280° C. and under from 5 to 150 bar; the pressure employed may also be greater than 200 bar; if necessary, the reaction is carried out under reduced pressure.

The novel process is carried out in general under superatmospheric pressure by a batchwise procedure, for example in an autoclave, or preferably continuously, for example in a tube reactor, the residence times being from 10 seconds to 3 hours, preferably from 1 minute to 2 hours.

To carry out the novel process by a continuous procedure, the compounds II or III and water with or without an acid or an alcohol with an acid are advantageously passed into the reactor, which has been heated to the reaction temperature, separately via separate feed lines, if necessary in the presence of an inert solvent. The reaction mixture is pumped through the reactor under superatmospheric pressure, then let down and cooled, after which it is worked up by conventional methods, such as phase separation, extraction and distillation.

In the batchwise procedure, the compounds II or III with water and, if required, an acid or with an alcohol and an acid, and in the presence or absence of an inert solvent, are heated to the reaction temperature, for example in a closed autoclave, and the mixture is then worked up in a conventional manner.

From 0.1 to 50, preferably from 0.5 to 20, particularly preferably from 1 to 10, moles of water or of an alcohol are used per mole of the compounds II or III.

Suitable alcohols are those of 1 to 20, preferably 1 to 8, particularly preferably 1 to 4, carbon atoms, such as methanol, ethanol and n-propanol.

Preferred acidic catalysts are homogeneous catalysts, such as inorganic acids, e.g. sulfuric acid, hydrochloric acid and phosphoric acid, and organic acids. Organic acids, such as carboxylic acids, e.g. formic acid, acetic acid and propionic acid, or sulfonic acids, e.g. methanesulfonic acid and p-toluenesulfonic acid, are particularly preferred.

When water is used, heterogeneous catalysts, e.g. silica, can also be employed.

When an alcohol is used, the amount of acid added is from 0.001 to 10, preferably from 0.01 to 1, particularly preferably from 0.1 to 0.5, mol %, based on compounds II or III. When water is used, the addition of an acid can be dispensed with; if necessary, a higher reaction rate and a slightly higher yield are obtained here by adding from 0.01 to 1 mol % of acid.

$R^1$ and $R^2$ in the compounds II have the following meanings, where $R^1$ and $R^2$ may furthermore be hydrogen:

straight-chain or branched $C_1$–$C_{10}$-alkyl, preferably $C_1$–$C_8$-alkyl, particularly preferably $C_1$–$C_4$-alkyl, such as methyl, ethyl, n-propyl, isopropyl, n-butyl, isobutyl, sec-butyl or tert-butyl, straight-chain or branched $C_1$–$C_{10}$-alkyl which is substituted by cycloaliphatic radicals, such as cycloalkyl, aromatic radicals, such as aryl, in particular phenyl, or heterocyclic radicals, such as pyridyl, by an alkenyl or alkynyl radical or by carbalkoxy, carboxyl, alkylamino, acyl, phosphonic ester, hydroxyl, ether, cycloether, thioether or cyclothioether groups, preferably $C_3$–$C_8$-cycloalkyl, $C_1$–$C_4$-carbalkoxy, carboxyl, or $C_2$–$C_4$-alkenyl, particularly preferably $C_5$- or $C_6$-cycloalkyl.

Preferred compounds I and II are those in which $R^1$ and $R^2$ are not hydrogen, particularly preferred compounds here in turn being those in which $R^1 = R^2$.

Starting materials of the formula II are, for example:
2,5-dimethyl-2-formyl-3,4-dihydropyran
2,5-diethyl-2-formyl-3,4-dihydropyran
2,5-di-n-propyl-2-formyl-3,4-dihydropyran
2,5-di-isopropyl-2-formyl-3,4-dihydropyran
2,5-di-n-butyl-2-formyl-3,4-dihydropyran
2,5-di-(3-methoxycarbonylpropyl)-2-formyl-3,4-dihydropyran
2,5-di-(methoxycarbonylmethyl)-2-formyl-3,4-dihydropyran
2-methyl-2-formyl-3,4-dihydropyran
5-methyl-2-formyl-3,4-dihydropyran
2,5-di-(2-propenyl)-2-formyl-3,4-dihydropyran.

Starting materials of the formula III are, for example:
methacrolein
ethacrolein
n-propylacrolein
isopropylacrolein
n-butylacrolein
(3-methoxycarbonylpropyl)-acrolein
methoxycarbonylmethylacrolein
(2-propenyl)-acrolein End products of the formula I of the novel process are:
2,5-dimethylcyclopentanone
2,5-diethylcyclopentanone
2,5-di-n-propylcyclopentanone
2,5-di-isopropylcyclopentanone
2,5-di-n-butylcyclopentanone
2,5-di-(3-methoxycarbonylpropyl)-cyclopentanone
2,5-di-(methoxycarbonylmethyl)-cyclopentanone
2-methyl-cyclopentanone
2,5-di-(2-propenyl)-cyclopentanone The cyclopentanones I are suitable, for example, as solvents (U.S. Pat. No. 2,875,249) or as intermediates for the synthesis of herbicides (U.S. Pat. No. 4,155,744), sweeteners (U.S. Pat. No. 4,692,513 and EP-A-34 876) and drugs (DE-A-2 344 527 and DE-A-1 670 753).

EXAMPLES

A: Preparation of 2-formyl-2,5-dimethylcyclopentanone from 2-formyl-2,5-dimethyl-3,4-dihydropyran (dimeric methacrolein)

EXAMPLE 1

60.4 g/hour of dimeric methacrolein were vaporized under atmospheric pressure and passed, together with 50 l/hour of nitrogen into a reactor (internal diameter of quartz tube 30 mm) which was heated at 200° C. and contained 200 ml of $SiO_2$ extrudates (3 mm diameter, bulk density 427 g/l). The reaction vapors formed were condensed. After operation for 13 hours, 774.4 g of reaction mixture having the following composition (quantitative GC analysis) were obtained:
  93.6% by weight of 2-formyl-2,5-dimethylcyclopentanone,
  2.0% by weight of 2,5-dimethylcyclopentanone and
  1.1% by weight of dimeric methacrolein.

This corresponds to a formylketone selectivity of 93.3% at 98.9% conversion. Fractional distillation gave a cis/trans mixture of the formylketone as a colorless liquid (bp. 96°-98° C./50 mbar).

EXAMPLE 2

51.4 g/hour of dimeric methacrolein were passed from an evaporator, under atmospheric pressure, together with 50 l/hour of nitrogen, into a reactor (internal diameter of quartz tube 30 mm) which was heated at 300° C. and contained 200 ml of a catalyst consisting of 20% by weight of $B_2O_3$ and 80% by weight of $SiO_2$ in the form of 3 mm extrudates having a bulk density of 624 g/l. The reaction vapors formed were condensed. After operation for 2.5 hours, 122.5 g of the reaction mixture having the following composition (quantitative GC analysis) were obtained:
  5.0% by weight of dimeric methacrolein,
  3.5% by weight of 2-formyl-2,5-dimethylcyclopentanone and
  3.6% by weight of 2,5-dimethylcyclopentanone.

This corresponds to a conversion of 95.2% and a formylketone selectivity of 83.7%.

EXAMPLE 3

That part of a V2A stainless steel tube (internal diameter 6 mm) which was filled with 7.0 ml of SiO₂ extrudates (3 mm diameter, bulk density 427 g/l) was heated at 180° C. in an oil bath. A solution of 50.6 g of dimeric methacrolein in 59.4 g of cyclohexane was passed, per hour, over the catalyst under 50 bar. After the pressure had been let down and the mixture cooled, 110.0 g/hour of reacted mixture which contained 31.6 g of 2-formyl-2,5-dimethylcyclopentanone and 16.5 g of dimeric methacrolein in addition to cyclohexane were obtained (quantitative GC analysis). This corresponds to a selectivity of 92.7% at 67.4% conversion.

B: Preparation of 2-formyl-2,5-diethylcyclpentanone from 2-formyl-2,5-diethyl-3,4-dihydropyran (dimeric ethylacrolein)

Example 4

49.3 g/hour of dimeric ethylacrolein were vaporized under atmospheric pressure and passed, together with 50 l/hour of nitrogen, into a reactor (internal diameter of quartz tube 30 mm) which was heated at 200° C. and contained 200 ml of SiO₂ extrudates having a diameter of 3 mm and a bulk density of 427 g/l. Condensation of the reaction vapors gave, after 16.5 hours, 808.5 g of reacted mixture which had the following composition (quantitative GC analysis):

4.0% by weight of 2-formyl-2,5-diethyl-3,4-dihydropyran,
  94.2% by weight of 2-formyl-2,5-diethylcyclopentanone and
  2.0% by weight of 2,5-diethylcyclopentanone.

This corresponds to a formylketone selectivity of 95.4% at a conversion of 96.0%.

Fractional distillation of the crude product gave pure 2-formyl-2,5-diethylcyclopentanone (cis-trans mixture), a colorless liquid of boiling point 128°–130° C./50 mbar).

C: Preparation of 2-formyl-2,5-diisopropylcyclopentanone from 2-formyl-2,5-diisopropyl-3,4-dihydropyran (dimeric isopropylacrolein)

Example 5

49.3 g/hour of dimeric isopropylacrolein and 50 liters/hour of nitrogen were passed under atmospheric pressure from an evaporator into a reactor (internal diameter of quartz tube 30 mm) heated at 200° C. and containing 200 ml of SiO₂ extrudates (diameter 3 mm, bulk density 427 g/l). The reaction vapors formed were condensed. Operation for 4 hours gave 193.5 g of reacted mixture which, according to quantitative GC analysis, contained 94.8% by weight of 2-formyl-2,5-diisopropylcyclopentanone and 4.3% by weight of 2,5-diisopropylcyclopentanone. For complete conversion of dimeric isopropylacrolein, this corresponds to a yield of formylketone of 93.0%. Fractional distillation gave pure 2-formyl-2,5-diisopropylcyclopentanone (cis/trans mixture (bp. 142°–143° C./20 mbar); 2,5-diisopropylcyclopentanone of boiling point 128°–133° C./50 mbar was obtained as a byproduct.

E: Preparation of 2,5-dimethylcyclopentanone from 2-formyl-2,5-dimethyl-3,4-dihydropyran (dimeric methacrolein)

Example 6

A solution of 23.0 g of dimeric methacrolein and 26.3 g of methanol was vaporized per hour under atmospheric pressure and passed, together with 25 l/hour of nitrogen, into a reactor (internal diameter of quartz tube 30 mm) heated at 250° C. and containing 200 ml of SiO₂ extrudates (3 mm diameter, bulk density 427 g/l). The reaction vapors formed were condensed. Operation for 2 hours gave 86.3 g of a reaction mixture which, according to quantitative gas chromatographic determination, contained 38.6% by weight of 2,5-dimethylcyclopentanone. This corresponds to a yield of 90.5% for complete conversion. Fractional distillation gave pure 2,5-dimethylcyclopentanone (cis/trans mixture, bp. 76°–86° C./100 mbar), in addition to methanol and methyl formate.

E: Preparation of 2,5-diethylcyclopentanone from 2-formyl-2,5-diethyl-3,4-dihydropyran (dimeric ethylacrolein)

Example 7

A solution of 24.2 g of dimeric ethylacrolein and 23.0 g of methanol was vaporized per hour under atmospheric pressure and passed, together with 25 l/h of nitrogen, into a reactor (internal diameter of quartz tube 30 mm) heated at 300° C. and containing 200 ml of SiO₂ extrudates (diameter 3 mm, bulk density 427 g/l). Condensation of the reaction vapors gave, after 3 hours, 129.5 g of a reacted mixture containing 44.8% by weight of 2,5-diethylcyclopentanone (quantitative gas chromatography). This corresponds to a yield of 96.9% for quantitative conversion. Fractional distillation of the crude product gave pure 2,5-diethylcyclopentanone (cis/trans mixture) as a colorless liquid of boiling point 54°–57° C./10 mbar, in addition to methanol and methyl formate.

F: Preparation of 2,5-di-n-propylcyclopentanone from 2-formyl-2,5-di-n-propyl-3,4-dihydropyran (dimeric n-propylacrolein)

Example 8

50 /h of nitrogen, as a fluidizing agent, were passed from below into a reactor (internal diameter of quartz tube 60 mm) heated at 250° C. and containing 300 ml of SiO₂ chips (0.1–0.3 mm, bulk density 363 g/l). A solution of 254.4 g of dimeric n-propylacrolein and 207.2 g of methanol was metered, in the course of 8 hours, directly into the fluidized bed through a metal capillary (at a distance of 1 cm from the lower end of the catalyst bed). Condensation of the reaction vapors gave 419.4 g of reacted mixture which contained 174.1 g of 2,5-di-n-propylcyclopentanone. For complete conversion of dimeric propylacrolein, this corresponds to a yield of 79.8%. Fractional distillation gave pure 2,5-din-propyl-cyclopentanone (cis/trans mixture, bp. 125°–128° C./50 mbar).

Comparative Examples

Example 9

(analogous to U.S. Pat. No. 3,812,190, Example 9)

25.4 g/hour of dimeric methacrolein were vaporized under atmospheric pressure and passed, together with 25 l/hour of nitrogen, into a reactor (internal diameter of quartz tube 27 mm) heated at 225° C. and containing 100 ml of a catalyst consisting of 0.72% by weight of Pd and 99.28% by weight of gamma-Al$_2$O$_3$ in the form of 4 mm extrudates having a bulk density of 690 g/l. The reaction vapors formed were condensed. Operation for 3 hours gave 47.7 g of a reaction mixture which, according to quantitative gas chromatographic determination, contained 21.0% by weight of 2,5-dimethylcyclopentanone. This corresponds to a yield of 16.4% for complete conversion.

Example 10

(analogous to U.S. Pat. No. 3,812,190, Example 9)

From an evaporator, 25.4 g/hour of dimeric methacrolein were passed, under atmospheric pressure, together with 25 l/hour of nitrogen, into a reactor (internal diameter of quartz tube 27 mm) heated at 225° C. and containing 100 ml of NiO pellets (3×3 mm, bulk density 2,330 g/l). The reaction vapors formed were condensed. Operation for 3 hours gave 69.8 g of reaction mixture which, according to quantitative gas chromatography, contained 92.4% by weight of dimeric methacrolein and 0.6% by weight of 2,5-dimethylcyclopentanone. This corresponds to a conversion of 15.4% and a selectivity of 4.5%.

G: Preparation of 2,5-dimethylcyclopentanone from 2,5-dimethyl-2-formyl-3,4-dihydropyran (dimeric methacroleins)

EXAMPLE 11

40.9 g of dimeric methacrolein and a solution of 110 mg of p-toluenesulfonic acid in 10.8 g of water were pumped, per hour, through a coiled tube having a length of 10 mm and an internal diameter of 2.17 mm, under 100 bar and at 250° C. At the reactor outlet, the reaction mixture was let down to atmospheric pressure and was cooled. After the aqueous phase had been evaporated off, 43.2 g/hour of organic phase remained; according to quantitative gas chromatography, the organic phase contained 57.4% by weight of 2,5-dimethylcyclopentanone. For complete conversion of the dimeric methacrolein, this corresponds to a yield of 75.8%. After operation for 5 hours, the organic phase was washed neutral with sodium hydroxide solution and subjected to fractional distillation; 121.5 g of 2,5-dimethylcyclopentanone (cis/trans mixture, bp. 76°–86° C./100 mbar) were obtained.

Example 12

482.4 g of dimeric methacrolein and a solution of 1.20 g of p-toluenesulfonic acid in 123.8 g of water were pumped, per hour, at 275° C., through the coiled tube, similarly to Example 11. According to quantitative gas chromatography of the organic phase of the reacted mixture, 279.2 g/hour of 2,5-dimethylcyclopentanone were obtained, corresponding to a yield of 72.3%.

Example 13

52.4 g of dimeric methacrolein and a solution of 70 g of p-toluenesulfonic acid in 29.6 g of methanol were pumped, per hour, at 275° C., through the coiled tube, as described in Example 11. Quantitative gas chromatographic analysis of the reacted mixture gave a yield of 25.4 g/hour of 2,5-dimethylcyclopentanone, corresponding to a yield of 60.6%.

Example 14

28.0 g of dimeric methacrolein were heated, together with 31 g of water, to 250° C. in the course of 4 hours in a closed autoclave (0.3 liter), while stirring, and left for 2 hours at this temperature. Cooling the reaction mixture gave 26.8 g of organic phase, which contained 14.6 g of 2,5-dimethylcyclopentanone; the yield was 65.2%.

H: Preparation of 2,5-dimethylcyclopentanone from methacrolein

Example 15

18.2 g of methacrolein and 4.7 g water were pumped, per hour, at 250° C., through the coiled tube, similarly to Example 11. After the aqueous phase had been separated off, 18.6 g/hour of organic phase remained; according to gas chromatographic determination, the organic phase contained 43.8% of 2,5-dimethylcyclopentanone corresponding to a yield of 61.7%.

Example 16

910 g of methacrolein and 234 g water were heated to 250° C. in the course of 3 hours in an autoclave (2.5 liters), while stirring, and were left at this temperature for 2 hours. The mixture was cooled, after which the aqueous phase was separated off and extracted with twice 50 ml of methyl tert-butyl ether. Fractional distillation of the combined organic phases gave 398.2 g of 2,5-dimethylcyclopentanone, corresponding to a yield of 54.7%.

I: Preparation of 2,5-diethylcyclopentanone from 2,5-diethyl-2-formyl-3,4-dihydropyran (dimeric ethylacrolein)

Example 17

88.7 g of dimeric ethylacrolein and a solution of 100 mg of p-toluenesulfonic acid in 21.3 g water were pumped, per hour, at 275° C., through the coiled tube, similarly to Example 11. 84.0 g/hour of organic phase were obtained; according to gas chromatography, the organic phase contained 51.6% by weight of 2,5-diethylcyclopentanone corresponding to a yield of 58.6%. Fractional distillation gave pure 2,5-diethylcyclopentanone as a cis/trans mixture (bp. 54°–57° C./10 mbar).

J: Preparation of 2,5-diisopropylcyclopentanone from 2,5-diisopropyl-2-formyl-3,4-dihydropyran (dimeric isopropylacrolein)

Example 18

99.2 g of dimeric isopropylacrolein and a solution of 500 mg of p-toluenesulfonic acid in 19.7 g water were pumped, per hour, through the coiled tube, heated at 285° C., as in Example 11. A quantitative gas chromatogram of the resulting organic phase indicated a yield of 46.9 g/hour of 2,5-diisopropylcyclopentanone (55.2% of theory), which was obtained as a colorless liquid of boiling point 128°–133° C./50 mbar after fractional distillation.

We claim:

1. A process for the preparation of a cyclopentanone of the formula

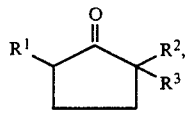

where $R^1$ and $R^2$ are each $C_1$–$C_{10}$-alkyl which is unsubstituted or substituted by a member selected from the group consisting of a cycloaliphatic, aromatic, heterocyclic, alkenyl or alknynyl radical or a carbalkoxy, carboxyl, alkaylamino, acyl, phosphonic ester, hydroxyl, ether, cycloether, thioether or cyclothioether group, or one of $R^1$ or $R^2$ may be hydrogen and $R^3$ is hydrogen or formyl, which process comprises:

reacting a 2-formyl-3,4-dihydropyran of the formula

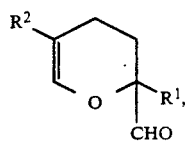

where $R^1$ and $R^2$ have the abovementioned meanings, by one of the processes:
a) to obtain product I where $R^3$ is formyl, by converting compound II in the presence of an acidic heterogeneous catalyst at from 50° to 500° C. in the liquid or gas phase; or
b) to obtain product I where $R^3$ is hydrogen, by reacting compound II with water or an alcohol in the presence of an acidic heterogeneous catalyst at from 100° to 500° C. in the gas phase, with the proviso that said acidic heterogeneous catalyst is selected from the group consisting of aluminum phosphates, silicon aluminum phosphates and the acidic oxides of elements of main groups II to V and subgroups III to VII of the Periodic Table and the acidic oxides of the rare earth metals, or mixtures of said oxides.

2. A process as claimed in claim 1, wherein the acid heterogeneous catalyst used is an acidic oxide selected from the group consisting of the oxides of elements of main groups II to V, subgroups III to VII and the rare earth metals of the Periodic Table, or mixtures thereof.

3. A process as claimed in claim 1, wherein the acidic heterogeneous catalyst used is silica.

4. A process as claimed in claim 1, wherein $R^1$ and $R^2$ are each $C_1$–$C_{10}$-alkyl which is unsubstituted or substituted by cycloaliphatic, aromatic or heterocyclic radicals, by an alkenyl or alkynyl radical or by carbalkoxy, carboxyl, alkylamino, acyl, hydroxyl, ether or thioether groups.

5. A process as claimed in claim 1, wherein $R^1$ and $R^2$ in the compounds have the same meaning.

6. A process b) as claimed in claim 1, wherein the molar ratio of water or of an alcohol to the 2-formyl-3,4-dihydropyran II is from 0.5:1 to 20:1.

7. A process as claimed in claim 1, wherein the molar ratio of water or of an alcohol to the 2-formyl-3,4-dihydropyran II is from 1:1 to 10:1.

8. A process as claimed in claim 1, wherein the organic radical designated for $R^1$ or $R^2$ is an unsubstituted $C_1$–$C_{10}$-alkyl.

9. A process as claimed in claim 1, wherein the organic radical designated for $R^1$ or $R^2$ is an unsubstituted $C_1$–$C_8$-alkyl.

10. A process as claimed in claim 1, wherein the organic radical designated for $R^1$ or $R^2$ is an unsubstituted $C_1$–$C_4$-alkyl.

11. A process for the preparation of a cyclopentanone of the formula

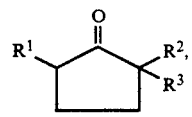

where $R^1$ and $R^2$ are each $C_1$–$C_{10}$-alkyl which is unsubstituted or substituted by a member selected from the group consisting of a cycloaliphatic, aryl, heterocyclic, alkenyl or alkynyl radical or a carbalkoxy, carboxyl, alkylamino, acyl, phosphonic ester, hydroxyl, ether, cycloether, thioether or cyclothioether group, or one of $R^1$ or $R^2$ may be hydrogen and $R^3$ is hydrogen, which process comprises:

reacting a 2-formyl-3,4-dihydropyran of the formula

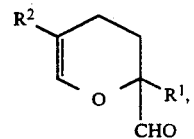

or an acrolein of the formula

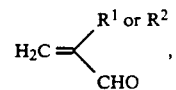

where $R^1$ and $R^2$ are each as defined above but not hydrogen, with water or with water in the presence of an organic acid or with an alcohol in the presence of an organic acid at from 200° to 400° C. in the liquid phase, with the proviso that the amount of acid used does not exceed about 0.01 to 1 mol %, based on the reactant II or III.

12. A process as claimed in claim 11, wherein the acid is an organic acid selected from the group consisting of carboxylic and sulfonic acids.

13. A process as claimed in claim 11, wherein $R^1$ and $R^2$ are each $C_1$–$C_6$-alkyl which is unsubstituted or substituted by a member selected from the group consisting of $C_3$–$C_8$-cycloalkyl, phenyl, pyridyl, $C_1$–$C_4$-carbalkoxy, carboxyl, and $C_2$–$C_4$-alkenyl.

14. A process as claimed in claim 11, wherein $R^1$ and $R^2$ in the compounds have the same meaning.

15. A process as claimed in claim 11, wherein the molar ratio of water or of an alcohol to the 2-formyl-3,4-dihydropyran II is from 0.1:1 to 50:1.

16. A process as claimed in claim 11, wherein the molar ratio of water or of an alcohol to the 2-formyl-3,4-dihydropyran II is from 0.5:1 to 20:1.

17. A process as claimed in claim 11, wherein the molar ratio of water or of an alcohol to the 2-formyl-3,4-dihydropyran II is from 1:1 to 10:1.

* * * * *